United States Patent [19]
Iritani et al.

[11] Patent Number: 5,854,368
[45] Date of Patent: *Dec. 29, 1998

[54] ADJUVANT FOR PHARMACEUTICAL PREPARATIONS

[75] Inventors: Koji Iritani; Tetsuya Kawasaki, both of Hyogo; Nobutaka Tani, Osaka; Shigeki Masuda; Yoshiaki Yano, both of Hyogo, all of Japan

[73] Assignee: Kanegafuchi Kagaku Kogyo Kabushiki Kaisha, Osaka, Japan

[*] Notice: The term of this patent shall not extend beyond the expiration date of Pat. No. 5,644,012.

[21] Appl. No.: 774,492

[22] Filed: Dec. 30, 1996

Related U.S. Application Data

[63] Continuation of Ser. No. 977,100, Nov. 16, 1992, Pat. No. 5,644,012.

[30] Foreign Application Priority Data

Nov. 15, 1991 [JP] Japan ..................... 3-300395
Nov. 26, 1991 [JP] Japan ..................... 3-310873

[51] Int. Cl.⁶ ............................................. C08G 63/668
[52] U.S. Cl. ..................... 527/311; 536/115; 536/119; 536/123.1
[58] Field of Search ..................... 527/311; 536/115, 536/119, 123.1

[56] References Cited

U.S. PATENT DOCUMENTS

| | | | |
|---|---|---|---|
| 2,823,188 | 1/1958 | Novak | 527/311 |
| 3,483,169 | 12/1969 | Case et al. | 527/311 |
| 3,663,463 | 5/1972 | Wren | 527/311 |
| 3,688,763 | 9/1972 | Cromarty | 128/759 |
| 3,756,966 | 9/1973 | Lamberti | 536/115 |
| 3,849,341 | 11/1974 | Lamberti | 536/115 |
| 3,862,121 | 1/1975 | Jaques et al. | 536/115 |
| 4,100,342 | 7/1978 | Finley | 536/115 |
| 4,124,571 | 11/1978 | Georgoudis | 527/311 |
| 4,151,304 | 4/1979 | Evans et al. | 536/116 |
| 4,155,884 | 5/1979 | Hughes | 527/311 |
| 4,713,436 | 12/1987 | Downs et al. | 527/300 |
| 5,283,064 | 2/1994 | Suzuki et al. | 424/451 |
| 5,294,448 | 3/1994 | Ring et al. | 424/497 |
| 5,354,559 | 10/1994 | Morehouse | 424/488 |
| 5,401,512 | 3/1995 | Rhodes et al. | 424/458 |
| 5,444,054 | 8/1995 | Garleb et al. | 514/54 |
| 5,525,634 | 6/1996 | Sintov et al. | 514/777 |
| 5,576,020 | 11/1996 | Iratani et al. | 424/465 |
| 5,644,012 | 7/1997 | Iratani et al. | 527/311 |

FOREIGN PATENT DOCUMENTS

| | | |
|---|---|---|
| 0398472 | 11/1990 | European Pat. Off. |
| 0450176 | 10/1991 | European Pat. Off. |
| 0542299 | 5/1993 | European Pat. Off. |
| 58-0072920A | 9/1983 | Japan |
| 60-0053-580-A | 3/1985 | Japan |
| 60-53580 | 3/1985 | Japan |
| 60-72920 | 4/1985 | Japan |

OTHER PUBLICATIONS

*Journal of Polymer Science: Polymer Chemistry Edition,* 18:365–370 (1980) International Search Report.

Saffran et al, "A New Approach to the Oral Administration of Insulin and Other Peptide Drugs", *Science,* 233:1081–1084 (Sep. 1986).

Kopecek et al, "Polymers for Colon–Specific Drug Delivery", *J. Controlled Release,* 19:121–130 (Feb. 1992).

Kurita et al, "Synthetic Polymers Containing Sugar Residues. V. Polyesters Derived from D–Cellobiose and Dicarboxylic Acid Chlorides by Direct Polycondensation", *J. Polym. Sci.: Polym. Chem. Ed.,* 18:365–370 (Jan. 1980).

Lancaster et al, "Drug Delivery to the Colon: Polymer Susceptibility to Degradation by Colon Contents", *Polymer Preprints,* 30(1):480–481 (Apr. 1989).

*Primary Examiner*—Jeffrey C. Mullis
*Attorney, Agent, or Firm*—Sughrue, Mion, Zinn, Macpeak & Seas, PLLC

[57] ABSTRACT

A polyester represented by the following general formula (I) and a copolymer which comprises two structural units represented by the following general formulae (I') and (II).

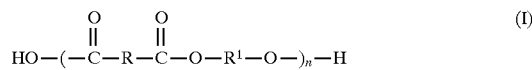

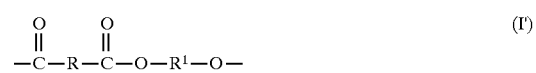

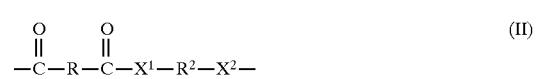

and a coating material for use in large intestine-selective drug release pharmaceutical preparations, which contains the above polyester and/or copolymer. The polyester and copolymer of the present invention contain a saccharide residue which is hydrolyzed and/or assimilated specifically in the large intestine, drugs contained in solid oral pharmaceutical administration pharmaceutical preparations coated with the coating material of the present invention are not decomposed or absorbed by digestive organs other than the large intestine, but instead are released selectively and therefore in a high concentration in the large intestine.

10 Claims, No Drawings

ADJUVANT FOR PHARMACEUTICAL PREPARATIONS

This is a continuation of U.S. application Ser. No. 07/977,100, filed Nov. 16, 1992 now U.S. Pat No. 5,644,012.

FIELD OF THE INVENTION

This invention relates to a polymer which is decomposed in the large intestine and to an adjuvant for pharmaceutical preparation use that contains the polymer as a main component. More particularly, it relates to a coating material of solid preparations for oral administration, that contains a polyester and/or a copolymer which is decomposed and/or assimilated in the large intestine by saccharolytic enzymes and the like.

BACKGROUND OF THE INVENTION

Intravenous injection is currently used as a means for the administrating protein and peptide drugs such as insulin, vasopressin and the like. With the increasing popularity of these protein and peptide drugs, attempts have been made to develop more simple means for their administration, such as oral, percutaneous, nasal, suppository and the like administration means. In particular, oral administration has been examined from various angles as the most common means. However, the bioavailability of protein and peptide drugs is extremely poor when they are administered orally, because these drugs are easily decomposed and inactivated by the enzymes in the small intestine.

As a result, attempts have been made to improve the bioavailability of these protein and peptide drugs by making these drugs into pharmaceutical preparations in such a manner that these drugs are selectively released in the large intestine where digestive enzymes are scarcely present.

For example, an enteric coated preparation has been developed which releases its drug contents due to melting of the coat when exposed to an increased pH. In some cases, however, such a preparation is decomposed in an upper portion of the small intestines, or is excreted without releasing its drug contents, because its decomposition is sensitive to intradiurnal changes in the pH in digestive tracts and diet.

As another type of large intestine-selective drug release preparations, attempts have been made to apply certain types of polymers which are selectively decomposed in the large intestine by the specific activity of enzymes secreted by bacteria in the large intestine. A large variety of anaerobic bacteria inhabit the large intestine and secrete various types of enzymes which are different from the human digestive enzymes. For example, an enzyme which is capable of reducing an azo group into its corresponding amino group is known to be a bacterial enzyme. Polymers containing aromatic azo groups which are hydrolyzed by the azo-reducing bacterial enzyme have been disclosed, for instance, in U.S. Pat. No. 4,663,308 and EP-A-398472 and CA-A-2012469 corresponding to JP-A-3-7718 (the term "JP-A" as used herein means an "unexamined published Japanese patent application"). The means described above, however, have the disadvantages that the polymers have poor coat formability and low solubility, and the azo group is carcinogenic.

SUMMARY OF THE INVENTION

With the aim of developing a high molecular weight compound for use as a coating which has excellent coat formability, is decomposed specifically in the large intestine and has high safety, the inventors of the present invention have conducted intensive studies and found that such properties can be achieved using a polyester with its principal chain containing a saccharide moiety which is hydrolyzed and/or assimilated in the large intestine, and from a copolymer containing such a saccharide and a desired compound. The present invention has been accomplished on the basis of this finding.

The present invention provides a polyester represented by the following formula (I):

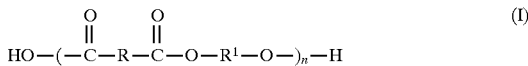

wherein R is a divalent organic group, $R^1$ is a saccharide residue which is hydrolyzed and/or assimilated in the large intestine, and n is an integer of 1 to 2,000, in which the structural units numbering n may be the same or different from one another. It also provides a coating material for use in large intestine-selective drug release pharmaceutical preparations, which contains the above polyester.

And there is provided a copolymer which comprises at least one structural unit represented by the following formula (I'):

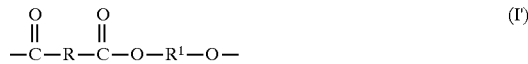

wherein R is a divalent organic group and $R^1$ is a saccharide residue which is hydrolyzed and/or assimilated in the large intestine; and at least one structural unit represented by the following formula (II):

wherein R is a divalent organic group, $X^1$ and $X^2$ are each independently an oxygen atom, an imino group or a sulfur atom, and $R^2$ is a group selected from the group consisting of saturated or unsaturated hydrocarbon having 1 to 20 carbon atoms, polyalkylene, polyalkylene glycol, polyarylene oxide, polyester and polyamide. It also provides a coating material which contains the above-mentioned copolymer for use in large intestine-selective drug release pharmaceutical preparations.

The polyester and copolymer of the present invention are described in detail as follows.

DETAILED DESCRIPTION OF THE INVENTION

The polyester of the present invention comprises a dibasic acid represented by HOOC—R—COOH and a saccharide represented by HO—$R^1$—OH, which are alternately bonded by ester linkage.

The copolymer of the present invention comprises the following structural units (I') and (II).

Though not particularly limited, the polymer may have a polyethylene glycol-based weight average molecular weight ranging preferably from 2,000 to 1,000,000, more preferably from 5,000 to 500,000, most preferably from 5,000 to 100,000.

The copolymerization ratio of the structural unit (I') to the structural unit (II) may be in the range of preferably from 1:99 to 99:1, more preferably from 5:95 to 80:20, most preferably from 10:90 to 70:30. The binding direction of the structural units (I') and (II) is not limited.

The structural unit represented by the formula (I') is obtained by subjecting a dibasic acid represented by HOOC—R—COOH and a saccharide represented by HO—R$^1$—OH to ester linkage reaction. Both ends of the copolymer of the present invention have independently a hydroxyl group, a carboxyl group, an amino group or a thiol group.

A large variety of bacteria inhabit the large intestine. Recent studies have revealed that these bacteria ferment and utilize certain saccharides which are not at all, or only slightly digestible and absorbable by the human body, and that such saccharides are actually absorbed by the living body through the action of these bacteria. In addition, studies on the formation of carcinogen in the human body have revealed the presence of specific saccharolytic enzymes in the large intestine, such as β-glucosidase, β-galactosidase, β-glucuronidase and the like, as well as polysaccharolytic enzymes such as xylanase, β-glucanase, galactomannase, polygalacturonase, mucinase, chondroitin lyase, carboxymethylcellulase, cellulase, polygalacturonate lyase and the like.

The saccharide represented by HO—R$^1$—OH is a slightly digestible saccharide which is hydrolyzed and/or assimilated in the large intestine, consisting of at least 2 saccharide residues but preferably 100 or less, more preferably 50 or less, and most preferably 10 or less. Examples of such saccharides include those which are hydrolyzed by the enzymes just described. The term "slightly digestible saccharide" as used herein means a saccharide which is not at all, or only slightly digested or absorbed in human small intestines. Though not particularly limited, illustrative examples of such slightly digestible saccharides include: galactooligosaccharides in which a few galactose molecules are linked to the galactose residue of lactose through β-1,4 or β-1,6 linkage, such as 6'-galactosyllactose, 4'-galactosyllactose and the like; fructooligosaccharides in which a few fructose molecules are linked to the fructose residue of sucrose through α-1 or β-2 linkage, such as 1-kestose, nistose and the like; soybean oligosaccharides in which a few galactose molecules are linked to the glucose residue of sucrose through β-1,6 linkage, such as raffinose, stachyose and the like; xylooligosaccharides in which a few xylose molecules are linked through β-1,4 linkage, such as xylobiose, xylotriose and the like; isomaltooligosaccharides in which a few glucose molecules are linked to the non-reducing glucose of isomaltose through α-1,4 or α-1,6 linkage, such as isomaltose, isomaltotriose, panose and the like; oligocelluloses in which a few glucose molecules are linked to cellulose through β-1,4 linkage, such as cellobiose, cellotriose and the like; lactose, lactosucrose, lacturose, paratinose, melezitose, turanose and melibiose; disaccharide alcohols such as maltitol, lactitol, isomaltitol, glucopyranosyl-α-1,6-mannitol and the like; and carboxymethyl cellulose, guar gum, tragacanth gum, xylan and the like.

Oligocelluloses such as cellobiose and raffinose are preferably used.

Preferred saccharide residue is hydrolyzed by β-glucosidase, β-galactosidase or β-glucuronidase.

Preferred examples of the saccharide residues are a galactooligosaccharide residue, a fructooligosaccharide residue and a soybean oligosaccharide residue.

These saccharides may be modified, for example, with acyl groups such as acetyl, benzoyl and the like, alkyl groups such as methyl, ethyl and the like, and hydroxyalkyl groups such as hydroxyethyl, hydroxypropyl and the like. The number of molecules of these modification groups to be linked to a saccharide molecule is not limited, provided that one saccharide molecule contains at least two remaining un-modified hydroxyl groups. The saccharide may be modified with a single group or with a plurality of different groups.

The polyester chain or copolymer of the present invention may contain two or more different types of the aforementioned saccharides, but preferably only a single type.

The divalent organic group represented by R is selected from the group consisting of m-phenylene group, p-phenylene group, 4,4'-biphenylene group, 2,6-naphthylene group, tetramethylene group, hexamethylene group, octamethylene group, decamethylene group, 3,3-pentylidene group, cis-ethenylene group, trans-ethenylene group or cyclohexylene group.

Though not particularly limited, the dibasic acid represented by HOOC—R—COOH may be selected from the group consisting of: aromatic dibasic acids such as terephthalic acid, isophthalic acid, 4,4'-dicarboxybiphenyl, 2,6-dicarboxynaphthalene, 1,2-bis(2-chlorophenoxy)ethane-4,4'-dicarboxylic acid and the like; aliphatic dibasic acids such as adipic acid, 1,10-decanedicarboxylic acid, diethylmalonic acid, fumaric acid, maleic acid, oxalic acid and the like; and dibasic acids of alicyclic compounds such as cyclohexane diacid and the like. The polyester chain or copolymer of the present invention may contain two or more different types of these dibasic acids, but preferably only a single type.

The structural unit represented by the formula (II) is obtained by linking the dibasic acid represented by HOOC—R—COOH to a compound represented by H—X$^1$—R$^2$—X$^2$—H, in which H—R$^2$—H is selected from the group consisting of saturated or unsaturated hydrocarbon, polyalkylene, polyalkylene oxide, polyarylene oxide, polyester and polyamide. The following describes the compound represented by H—X$^1$—R$^2$—X$^2$—H, with illustrative examples which are divided into 4 types (formulae III to VIII).

(1) A compound represented by the following formula (III):

$$H-X^1-R^3-X^2-H \qquad (III)$$

wherein $X^1$ and $X^2$ are each independently an oxygen atom, an imino group or a sulfur atom, and $R^3$ is a saturated or unsaturated hydrocarbon group having 1 to 20 carbon atoms. $R^3$ is preferably an ethylene group, a propylene group or a tetramethylene group. That is, a saturated or unsaturated hydrocarbon moiety, each of its ends independently having a hydroxyl group, an amino group or a thiol group. Illustrative examples of such compounds include: alkylene glycols such as ethylene glycol, propylene glycol, 1,2-butanediol, 1,3-butanediol, 1,4-butanediol and the like; alkylenediamines such as hexamethylenediamine, ethylenediamine, tetramethylenediamine and the like; alkanedithiol such as 1,4-butanedithiol, ethanedithiol and the like; aromatic diols such as 1,4-hydroquinone, 1,3-hydroquinone, 2,7-dihydroxy-naphthalene, catechol, 1,3-di(hydroxymethyl)benzene and the like; and aromatic diamines such as 1,4-diaminobenzene, 3,5-diaminotoluene and the like. These compounds are commercially available from, for example, Wako Pure Chemical Industries, Ltd.

(2) A compound represented by the following formula (IV):

wherein $X^1$ and $X^2$ are each independently an oxygen atom, an imino group or a sulfur atom, $R^4$ and $R^5$ are each independently an alkylene having 1 to 10 carbon atoms or aryl group having 6 to 10 carbon atoms, and n is an integer of 1 to 100. $R^4$ is preferably an ethylene group, a propylene group or a tetramethylene group and $R^5$ is preferably an ethylene group, a propylene group or a tetramethylne group. That is, a polyalkylene glycol or a polyarylene oxide, both ends of which have a hydroxyl group, an amino group or a thiol group. Illustrative examples of such a type of compounds include a polyethylene glycol, a polypropylene glycol, a polytetramethylene glycol and a polyphenylene oxide, wherein each end of these compounds have a hydroxyl group, an amino group or a thiol group.

A polypropylene glycol (PPG) and a polytetramethylene glycol (PTMG) are preferably used. Commercial products can be used as these compounds, for example, Polyethylene glycol 1000 (Wako Pure Chemical Industries, Ltd.), Tetrathane 650 (polytetramethylene glycol, by Du Pont) and PTG-DA-1000-1001 (polytetramethylene glycol whose both ends are amines, by Hodogaya Chemical Co., Ltd.).

(3) A compound represented by the following formula (V) or (VI):

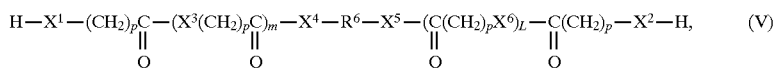

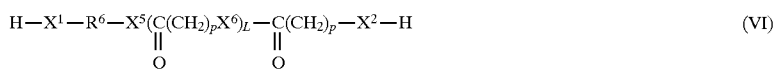

wherein $X^1$, $X^2$, $X^4$ and $X^5$ are each independently an oxygen atom, an imino group, or a sulfur atom, $X^3$ and $X^6$ are each independently an oxygen atom or an imino group, $R^6$ is an alkylene group having 1 to 20 carbon atoms, a divalent group of an aromatic compound having 6 to 20 carbon atoms or an alkylene glycol moiety having 1 to 20 carbon atoms, m and L are each independently an integer of 0 to 100, and p is an integer of 1 to 12; or a compound represented by the following formula (VII):

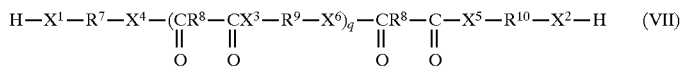

wherein $X^1$, $X^2$, $X^4$ and $X^5$ are each independently an oxygen atom, an imino group, or a sulfur atom, $X^3$ and $X^6$ are each independently an oxygen atom or an imino group, $R^7$, $R^9$ and $R^{10}$ are each independently an alkylene group having 1 to 20 carbon atoms or a divalent group of an aromatic compound having 6 to 20 carbon atoms, $R^8$ is a divalent organic group, and q is an integer of 1 to 100. $R^8$ may be the same or different as R.

In the above formulae (V), (VI) and (VII), $R^6$ is preferably an ethylene group, a tetramethylene group or a phenylene group, $R^7$ is preferably an ethylene group, a propylene group or a tetramethylene group, $R^8$ is preferably a phenylene group, a tetramethylene group, $R^9$ is preferably an ethylene group, a propylene group or a tetramethylene group and $R^{10}$ is preferably an ethylene group, a propylene group or a tetramethylene group. A polyester with each of its ends independently having a hydroxyl group, an amino group or a thiol group when $X^3$ and $X^6$ are oxygen atoms, wherein illustrative examples of such compounds include a poly-ε-caprolactone, a polyglycolic acid, a polylactic acid, a polyethylene terephthalate, polybutylene terephthalate and a polyethylene adipate, each of their chain ends independently having a hydroxyl group, an amino group or a thiol group; or a polyamide with each of its ends independently having a hydroxyl group, an amino group or a thiol group when $X^3$ and $X^6$ are imino groups, wherein illustrative examples of such compounds include a poly-ε-caprolactam and a hexamethylenediamine-adipic acid copolymer, each of their chain ends independently having a hydroxyl group, an amino group or a thiol group.

A poly-ε-caprolactone, a polyglycolic acid, a polylactic acid, polyethylene terephthalate and polybutylene terephthalate are preferably used in the present invention.

The compound represented by the formula (V) can be obtained by ring openning polymerization of caprolactone and the like using ethylene glycol and the like as an initiator.

The compound represented by the formula (VI) can be obtained by ring openning polymerization of caprolactone and the like using ethylene glycol and the like whose one end is protected as an initiator followed by removing the protecting group.

The compound represented by the formula (VII) can be obtained by subjecting a dibasic acid and ethylene glycol, ethylenediamine or the like to condensation.

(4) A compound represented by the following formula (VIII):

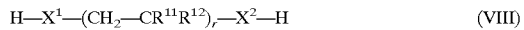

wherein $X^1$ and $X^2$ are each independently an oxygen atom, an imino group, or a sulfur atom, $R^{11}$ and $R^{12}$ are each independently a hydrogen atom, an alkyl group, an acetyl group, a phenyl group, a phenyl group substituted with 1 to 4 alkyl or nitro groups, a naphthalene group, a carboxyl group, a carboxymethyl group, a carboxyethyl group, a carboxyisopropyl group, a carboxy-2-hydroxyethyl group, a carboxy-2-hydroxypropyl group, a methoxycarbonyl group, an ethoxycarbonyl group, an isopropoxycarbonyl group, a 1-hydroxyethoxycarbonyl group or a 2-hydroxypropoxycarbonyl group, and r is an integer of 1 to 1,000. That is, a polyalkylene with each of its ends independently having a hydroxyl group, an amino group or a thiol group. An alkyl group represented by $R^{11}$ or $R^{12}$ have 1 to 10 carbon atoms. A phenyl group substituted with 1 to 4 alkyl or nitro groups and a naphthalene group represented by $R^{11}$ or $R^{12}$ have 6 to 20 carbon atoms in total, respectively.

Preferably, $R^{11}$ and $R^{12}$ are each independently a hydrogen atom, a methyl group, a hydroxyethyl group, a carboxymethyl group or a phenyl group.

Illustrative examples of such compounds include compounds of polystyrene, polyvinyl acetate, poly methyl methacrylate, poly hydroxyethyl methacrylate and the like, each of their chain ends independently having a hydroxyl group, an amino group or a thiol group.

Though the H—X$^1$—R$^2$—X$^2$—H compounds are not limited to the above illustrative examples, a polyether such as a polypropylene glycol or a polytetramethylene glycol with its chain ends being hydroxyl groups, or a polyester such as a poly-ε-caprolactone or a polyglycolic acid with its chain ends being hydroxyl groups may be most preferable in view of improved solubility in solvents and high safety.

The polyester and copolymer of the present invention having the aforementioned structural units can be synthesized for instance, in accordance with the procedure of Kurita, K. et al (Journal of Polymer Chemistry Edition, vol.18, p.365, 1980). That is, a saccharide is allowed to react with the compound to be copolymerized and/or a dibasic acid chloride at about 17° C. in an aprotic polar solvent such as N,N-dimethylacetamide (DMAc), dimethylsulfoxide (DMSO) or the like, using a tertiary amine such as pyridine, triethylamine or the like as a deprotonating agent.

The polyester and copolymer of the present invention can be used together in one composition.

Also included in the present invention is a coating material for pharmaceutical preparation use which contains the polyester or copolymer of the present invention, which has been described previously. Since the polyester and copolymer of the present invention are decomposed and/or assimilated specifically in the large intestine, they are useful as coating materials for pharmaceutical preparations which can used in order to prevent the drugs contained in such preparations from being decomposed by digestive enzymes since the coating materials of the present invention selectively release the drugs in the large intestines, and can improve the bioavailability of the drugs by accelerating their absorption from the large intestine due to their high concentration in the large intestine. The coating materials for pharmaceutical preparation use according to the present invention may contain base materials for use in dermatologic coat forming agents and drug-containing sheet-shaped agents for oral administration solid preparations, such as tablets, granules, pills, capsules and the like.

Drugs which can be made into pharmaceutical preparations which use the coating material of the present invention are not particularly limited, provided that their target organ is the large intestine. Illustrative examples of such a type of drugs include: peptides such as insulin, vasopressin, calcitonin, interferon, interleukin and the like; guanidinobenzoic acid derivatives such as mesyl gabexate, mesyl camostat, mesyl nafamostat and the like; or anti-inflammatory agents such as aspirin and the like.

When used as a dermatologic coat forming agent, the polyester or copolymer of the present invention is dissolved or suspended in an appropriate solvent or a mixture of two solvents which are selected, for example, from the group consisting of methylene chloride, acetone and ethanol, and the thus prepared solution or suspension is used to coat a separately prepared oral administration solid pharmaceutical preparation by the known means of pan coating, fluidized coating or the like. If necessary, the polyester or copolymer of the present invention may be mixed with a water insoluble polymer such as ethyl cellulose, a methacrylic copolymer or the like, and a plasticizer such as polyethylene glycol or the like.

Specific examples of the water insoluble polymers include ethyl cellulose, methacrylic acid copolymer and shellac.

Specific examples of the plasticizer include polyethylene glycol (PEG), glyceric acid ester, saccharose ester, castor oil, triethyl citrate and triacetin.

Tablet can be coated with a coating material of the present invention according to the following procedures.

A coating solution, which is prepared by dissolving the copolymer of the present invention in a methanol/methylene chloride mixture (1:1 by volume) to a final concentration of the copolymer of 5% by weight, was spray coated on raw tablet incorporated in pan coating which is revolving at 6 rpm to prepare the film coating tablet having a thickness of 100 to 200 μm.

When applied to a sheet-shaped pharmaceutical preparation, the drug to be included in the preparation and the polyester or copolymer of the present invention are suspended and mixed in an appropriate solvent as described above, the thus prepared mixture is made into a film using a film making machine in the usual way and then the resulting film is pulverized and packed into gelatin capsules and the like. If necessary, when the film is prepared, the polyester or copolymer of the present invention may be mixed with a water insoluble polymer such as ethyl cellulose, a methacrylic copolymer or the like, an enteric polymer such as hydroxypropylmethyl cellulose acetate succinate, carboxyethyl cellulose or the like, and a plasticizer such as polyethylene glycol or the like. Another pharmaceutical preparation can be obtained by making the polyester or copolymer of the present invention into a sheet or film without mixing a drug. Then the drug in the form of liquid or granules was put between thus-obtained sheets or films, followed by fusing these sheets or films to formulate into a dosage form such as a gelatin soft capsule.

The following examples are provided to further illustrate the polyester, the copolymer and the coating material of the present invention for use in large intestine-selective drug release pharmaceutical preparations. It is to be understood, however, that the examples are for purpose of illustration only and are not intended as a definition of the limits of the invention.

EXAMPLE 1

A 684 mg of lactose (2.0 mmol) and 0.32 ml of pyridine (4.0 mmol) were added to 10 ml of DMAc, and the mixture was stirred at 17° C. To this was added 406 mg of terephthalic acid dichloride (2.0 mmol). After 24 hours of reaction with stirring, gelatinized materials and unreacted lactose were removed by filtration, the resulting filtrate was poured into chloroform, and the thus formed precipitate was washed with chloroform and water. After drying the resulting washed precipitate under a reduced pressure, 820 mg of the product of interest was obtained with a yield of 87%.

The resulting product was checked by its NMR spectrum using DMSO-d$_6$ as a solvent, thereby confirming the presence of lactose and terephthalic acid in a ratio of about 1:1. Also, the molecular weight of the product was measured by subjecting it to gel permeation chromatography (GPC) using N,N-dimethylformamide (DMF) as a solvent, which showed that the product had a weight average molecular weight of 4,800 using a polyethylene glycol as a standard (hereinafter "polyethylene glycol-based weight average molecular weight").

$^1$H-NMR spectrum (δ, DMSO-d$_6$) chemical shifts: 3.1–5.8 (4.8 H), 7.8–8.3 (1 H)

EXAMPLE 2

The procedure of Example 1 was repeated except that 1,332 mg (2.0 mmol) of stachyose was used instead of lactose, thereby obtaining 1,380 mg (yield, 86%) of a product of interest having a polyethylene glycol-based weight average molecular weight of 6,800.

$^1$H-NMR spectrum (δ, DMSO-d$_6$) chemical shifts: 3.1–5.6 (9.8 H), 7.8–8.2 (1 H)

EXAMPLE 3

The procedure of Example 1 was repeated except that 684 mg (2.0 mmol) of cellobiose was used instead of lactose, thereby obtaining 800 mg (yield, 85%) of a product of interest having a polyethylene glycol-based weight average molecular weight of 5,200.

$^1$H-NMR spectrum ($\delta$, DMSO-$d_6$) chemical shifts: 3.0–5.5 (4.9 H), 7.8–8.3 (1 H)

EXAMPLE 4

The procedure of Example 1 was repeated except that 1,010 mg (2.0 mmol) of 6'-galactosyllactose was used instead of lactose, thereby obtaining 1,100 mg (yield, 86%) of a product of interest having a polyethylene glycol-based weight average molecular weight of 6,400.

$^1$H-NMR spectrum ($\delta$, DMSO-$d_6$) chemical shifts: 3.0–5.4 (7.3 H), 7.9–8.2 (1 H)

EXAMPLE 5

The procedure of Example 1 was repeated except that 1,010 mg (2.0 mmol) of 1-kestose was used instead of lactose, thereby obtaining 1,130 mg (yield, 89%) of a product of interest having a polyethylene glycol-based weight average molecular weight of 5,500.

$^1$H-NMR spectrum ($\delta$, DMSO-$d_6$) chemical shifts: 3.1–5.5 (7.4 H), 7.8–8.3 (1 H)

EXAMPLE 6

The procedure of Example 1 was repeated except that 366 mg (2.0 mmol) of adipic acid dichloride was used instead of terephthalic acid dichloride, thereby obtaining 650 mg (yield, 82%) of a product of interest having a polyethylene glycol-based weight average molecular weight of 3,400.

$^1$H-NMR spectrum ($\delta$, DMSO-$d_6$) chemical shifts: 1.7 (1 H), 2.5 (1 H), 3.2–5.3 (4.9 H)

REFERENCE EXAMPLE 1

A mixture consisting of 2% of Blue Dextran 2000, 2% of dextran, 2% of Alcian Blue 8GS, 2% of Aniline Blue, 2% of Methylene Blue, 3% of magnesium stearate and 87% of Avicel PH-102 (Asahi Kasei Kogyo Kabushiki Kaisha) was prepared and made into pigment-containing tablets, using a tablet machine (Model HU-T, Hata Iron Works Co., Ltd.) under the following conditions: punching die diameter, 4 mm; suction weight, 30 mg; revolving speed, 8.8 rpm; and punching pressure, 900 kg.

EXAMPLE 7

500 mg of each of the polyester samples obtained in Examples 1 to 6 was mixed with 500 mg of polyethylene glycol having a molecular weight of 4,000, and the resulting mixtures were each suspended in a methanol/methylene chloride mixture (1:1 by volume) to a final concentration of 10%. The pigment-containing tablets obtained in Reference Example 1 were soaked in the resulting suspension, and then dried. The soaking/drying step was repeated until the coated layer had a thickness of 100 to 200 $\mu$m, which was calculated based on the difference in the diameter and thickness of each tablet before and after the coating.

As a control, coated tablets were prepared by repeating the same procedure except that 500 mg of hydroxypropyl-methyl cellulose phthalate (HP-55S, Shin-Etsu Chemical Co., Ltd.), known as an enteric coating material, was used instead of the polyester of the present invention.

TEST EXAMPLE 1

The preparations obtained in Example 7 were checked for their disintegration and elution in vivo.

Experiments were carried out using eight-week-old male Wistar rats, with 4 to 6 individuals per group.

Each rat in the first group was subjected to ventrotomy to ligate the coaptating part of small intestines and the large intestine. The small intestine-side of the ligated portion was incised while the large intestine-side was returned into the abdominal area, and the incised portion of small intestines and the sectioned abdominal portion were sutured in such a manner that the intestinal tract remained open to the external area of the body. Next, the left side portion of the abdomen was opened by section to incise the uppermost portion of the duodenum (just below the gastric pylorus), and a coated tablet obtained in Example 7 was administered to the duodenum through the incised part. Thereafter, the incised portion was sutured and adhered using a surgical adhesive and the sectioned abdominal part was sutured. The thus treated rats were kept in a clean environment, and the contents discharged from the opened portion of the small intestine were observed in order to determine the presence of the tablet, the shape and hardness of the discharged tablet, and elution of pigment.

In each rat of the second group, the coaptating part of the small and large intestines was incised in the same manner as that of the first group, and then repaired by suturing, followed by the administration of three coated tablets obtained in Example 7 into the duodenum through its uppermost portion. The thus treated rats were kept in the same manner previously described, and the conditions of these rats' feces (color and contents) were examined.

In the third group, each rat was subjected to ventrotomy, the coaptating part of the small and large intestines was incised and the coated tablet obtained in Example 7 was inserted into the large intestine. After suturing the incised part and opened abdominal part, the thus treated rat was kept in the same manner to observe conditions of feces. The results are shown in Table 1.

TABLE 1

| Polymer | Film thickness ($\mu$m) | First group | Second group | Third group |
|---|---|---|---|---|
| Ex. 1[*1] | 100–120 | shaped[*2] some color[*4] | shapeless[*3] colored feces | shaped colored feces |
| Ex. 2 | 110–130 | shaped some color | shapeless colored feces | shapeless colored feces |
| Ex. 3 | 100–110 | shaped no color[*5] | shapeless colored feces | shapeless colored feces |
| Ex. 4 | 150–170 | shaped no color | shapeless colored feces | shaped colored feces |
| Ex. 5 | 140–160 | shaped no color | shapeless colored feces | shapeless colored feces |
| Ex. 6 | 120–140 | shaped some color | shapeless colored feces | shapeless colored feces |
| HP-55S | 125–130 | shapeless color[*6] | shapeless colored feces | shapeless colored feces |

Note:
[*1], Inventive Example;
[*2], shape of tablet remained;
[*3], shape of tablet did not remain;
[*4], contents slightly colored;
[*5], contents not colored;
[*6], contents colored

EXAMPLE 8

A 684 mg of lactose (2.0 mmol), 2.0 g (2.0 mmol) of polytetramethylene glycol (PTMG; avarage molecular weight, 1,000) and 0.64 ml of pyridine (8.0 mmol) were added to 20 ml of DMAc, and the mixture was stirred at 17° C. To this was added 812 mg of terephthalic acid dichloride (4.0 mmol). After 24 hours of reaction with stirring, gelatinized materials and unreacted lactose were removed by filtration, the filtrate was poured in water, and the resulting precipitate was washed with water. After drying the washed precipitate under reduced pressure, the resulting residue was again dissolved in DMAc, precipitated in water, washed with water and then dried. In this way, 2.56 g of a product of interest was obtained with a yield of 80%.

The resulting product was subjected to NMR spectrum analysis using DMSO-$d_6$ as a solvent, IR spectrum analysis and elementary analysis, thereby confirming the presence of lactose and PTMG in a ratio of about 1:2. Also, the molecular weight of the product was measured by subjecting it to gel permeation chromatography (GPC) using N,N-dimethylformamide (DMF) as a solvent, which showed that the product had a polyethylene glycol-based weight average molecular weight of 19,000.

$^1$H-NMR spectrum ($\delta$, DMSO-$d_6$) chemical shifts: 3.1–5.8 (4.9 H), 1.5 (24.1 H), 1.6 (2 H), 1.7 (2 H), 3.3 (25.8 H), 4.3 (2 H), 7.8–8.3 (3 H)

IR peaks (cm$^{-1}$): 3300, 2900, 2820, 1720, 1370, 1270, 1100

Elementary analysis: C: 63.76%, H: 9.20%

EXAMPLE 9

The procedure of Example 8 was repeated except that 1,332 mg (2.0 mmol) of stachyose was used instead of lactose, thereby obtaining 3.02 g (yield, 78%) of a product of interest having a polyethylene glycol-based weight average molecular weight of 18,000.

$^1$H-NMR spectrum ($\delta$, DMSO-$d_6$) chemical shifts: 3.1–5.8 (9.8 H), 1.5 (23.8 H), 1.6 (2 H), 1.7 (2.1 H), 3.3 (26.2 H), 4.3 (2 H), 7.7–8.3 (3 H)

IR peaks (cm$^{-1}$): 3300, 2910, 2830, 1730, 1370, 1260, 1100

Elementary analysis: C: 61.81%, H: 8.95%

EXAMPLE 10

The procedure of Example 8 was repeated except that 684 mg (2.0 mmol) of cellobiose was used instead of lactose, thereby obtaining 2.61 g (yield, 81%) of a product of interest having a polyethylene glycol-based weight average molecular weight of 20,000.

$^1$H-NMR spectrum ($\delta$, DMSO-$d_6$) chemical shifts: 3.1–5.8 (5.1 H), 1.5 (24.2 H), 1.6 (1.9 H), 1.7 (2 H), 3.3 (25.9 H), 4.3 (2 H), 7.8–8.2 (3.1 H)

IR peaks (cm$^{-1}$): 3300, 2900, 2810, 1720, 1360, 1270, 1100

Elementary analysis: C: 63.85%, H: 9.27%

EXAMPLE 11

The procedure of Example 8 was repeated except that 1,010 mg (2.0 mmol) of 6'-galactosyllactose was used instead of lactose, thereby obtaining 2.81 g (yield, 79%) of a product of interest having a polyethylene glycol-based weight average molecular weight of 17,000.

$^1$H-NMR spectrum ($\delta$, DMSO-$d_6$) chemical shifts: 3.1–5.7 (7.5 H), 1.5 (23.8 H), 1.6 (2.1 H), 1.7 (2 H), 3.3 (25.7 H), 4.3 (2 H), 7.7–8.2 (3.1 H)

IR peaks (cm$^{-1}$): 3300, 2910, 2820, 1725, 1380, 1270, 1100

Elementary analysis: C: 62.75%, H: 9.10%

EXAMPLE 12

The procedure of Example 8 was repeated except that 1,010 mg (2.0 mmol) of 1-kestose was used instead of lactose, thereby obtaining 2.79 g (yield, 79%) of a product of interest having a polyethylene glycol-based weight average molecular weight of 19,000.

$^1$H-NMR spectrum ($\delta$, DMSO-$d_6$) chemical shifts: 3.0–5.8 (7.4 H), 1.5 (24.2 H), 1.6 (2 H), 1.7 (2.2 H), 3.3 (25.8 H), 4.3 (2 H), 7.8–8.3 (2.8 H)

IR peaks (cm$^{-1}$): 3300, 2900, 2830, 1730, 1370, 1280, 1090

Elementary analysis: C: 62.65%, H: 9.22%

EXAMPLE 13

The procedure of Example 8 was repeated except that 366 mg (2.0 mmol) of adipic acid dichloride was used instead of terephthalic acid dichloride, thereby obtaining 2.35 g (yield, 75%) of a product of interest having a polyethylene glycol-based weight average molecular weight of 14,000.

$^1$H-NMR spectrum ($\delta$, DMSO-$d_6$) chemical shifts: 3.2–5.3 (4.8 H), 1.5 (24.2 H), 1.6 (2.1 H), 1.7 (1.9 H), 3.3 (25.8 H), 4.3 (2 H), 1.8 (3.1 H), 2.5 (3 H)

IR peaks (cm$^{-1}$): 3310, 2880, 2830, 1710, 1375, 1270, 1100

Elementary analysis: C: 62.57%, H: 9.91%

EXAMPLE 14

The procedure of Example 8 was repeated except that 2,000 mg (2.0 mmol) of poly-$\epsilon$-caprolactone having hydroxyl groups on both chain ends (average molecular weight, 1,000) was used instead of PTMG, thereby obtaining 2.55 g (yield, 79%) of a product of interest having a polyethylene glycol-based weight average molecular weight of 17,000.

$^1$H-NMR spectrum ($\delta$, DMSO-$d_6$) chemical shifts: 3.1–5.3 (4.8 H), 1.3 (8.1 H), 1.6 (16.3 H), 2.2 (8.2 H), 4.0 (7.9 H), 4.1 (2 H), 7.9–8.2 (3.3 H)

IR peaks (cm$^{-1}$): 3300, 2940, 2820, 1730, 1370, 1265, 1165, 1090

Elementary analysis: C: 59.61%, H: 8.01%

EXAMPLE 15

The procedure of Example 8 was repeated except that 2,000 mg (2.0 mmol) of poly-$\epsilon$-caprolactam having amino groups on both chain ends (average molecular weight, 1,000) was used instead of PTMG, thereby obtaining 2.44 g (yield, 76%) of a product of interest having a polyethylene glycol-based weight average molecular weight of 18,000.

$^1$H-NMR spectrum ($\delta$, DMSO-$d_6$) chemical shifts: 3.2–5.3 (5.1 H), 1.2 (7.9 H), 1.5 (15.9 H), 2.3 (7.8 H), 3.0 (8 H), 4.1 (2.1 H), 5.5 (4 H), 7.8–8.3 (2.9 H)

IR peaks (cm$^{-1}$): 3300, 2930, 2820, 1730, 1640, 1545, 1375, 1270, 1170, 1100

Elementary analysis: C: 60.01%, H: 8.73%

EXAMPLE 16

The procedure of Example 8 was repeated except that 2,000 mg (2.0 mmol) of poly methyl methacrylate having hydroxyl groups on both chain ends (average molecular weight, 1,000) was used instead of PTMG, thereby obtaining 2.32 g (yield, 72%) of a product of interest having a polyethylene glycol-based weight average molecular weight of 15,000.

$^1$H-NMR spectrum (δ, DMSO-d$_6$) chemical shifts: 3.2–5.4 (9.8 H), 1.15 (29.7 H), 1.2 (18.5 H), 3.7 (29.5 H), 4.1 (1.1 H), 7.9–8.3 (6.1 H)

IR peaks (cm$^{-1}$): 3300, 2950, 2815, 1730, 1540, 1450, 1370, 1275, 1150, 1095, 750

Elementary analysis: C: 56.79%, H: 7.31%

EXAMPLE 17

500 mg of each of the copolymer samples obtained in Examples 8 to 16 was mixed with 500 mg of polyethylene glycol having a molecular weight of 4,000, and the resulting mixture were each dissolved in a methanol/methylene chloride mixture (1:1 by volume) to a final concentration of 10%. The pigment-containing tablets obtained in Reference Example 1 were soaked in the resulting suspensions, and then dried. The soaking/drying step was repeated until the coated layer had a thickness of 100 to 200 μm, which was calculated based on the difference in the diameter and thickness of each tablet before and after the coating.

As a control, coated tablets were prepared by repeating the same procedure except that 500 mg of hydroxypropylmethyl cellulose phthalate (HP-55S, Shin-Etsu Chemical Co., Ltd.), known as an enteric coating material, was used instead of the copolymer of the present invention.

TEST EXAMPLE 2

The preparations obtained in Example 17 were checked for their disintegration and elution in vivo.

Experiments were carried out using eight-week-old male Wistar rats, with 4 to 6 individuals per group.

Each rat in the first group was subjected to ventrotomy to ligate the coaptating part of small intestines and the large intestine. The small intestine-side of the ligated portion was incised while the large intestine-side was returned into the abdominal area, and the incised portion of small intestines and the sectioned abdominal portion were sutured in such a manner that the intestinal tract remained open to the external area of the body. Next, the left side portion of the abdomen was opened by section to incise the uppermost portion of the duodenum (just below the gastric pylorus), and a coated tablet obtained in Example 17 was administered to the duodenum through the incised part. Thereafter, the incised portion was sutured and adhered using a surgical adhesive and the sectioned abdominal part was sutured. The thus treated rats were kept in a clean environment, and the contents discharged from the opened portion of the small intestine were observed in order to determine the presence of the tablet, the shape and hardness of the discharged tablet, and elution of pigment.

In each rat of the second group, the coaptating part of the small and large intestines was incised in the same manner as that of the first group and then repaired by suturing, followed by the administration of three coated tablets obtained in Example 17 into the duodenum through its uppermost portion. The thus treated rats were kept in the same manner previously described, and the conditions of these rats' feces (color and contents) were examined.

In the third group, each rat was subjected to ventrotomy, the coaptating part of the small and large intestines was incised and the coated tablet obtained in Example 17 was inserted into the large intestine. After suturing the incised part and opened abdominal part, the thus treated rat was kept in the same manner to observe conditions of feces.

The results are shown in Table 2.

TABLE 2

| Polymer | Film thickness (μm) | First group | Second group | Third group |
|---|---|---|---|---|
| Ex. 8*$^1$ | 100–120 | shaped*$^2$ some color*$^4$ | shapeless*$^3$ colored feces | shaped colored feces |
| Ex. 9 | 110–130 | shaped some color | shapeless colored feces | shapeless colored feces |
| Ex. 10 | 100–110 | shaped no color*$^5$ | shapeless colored feces | shapeless colored feces |
| Ex. 11 | 150–170 | shaped no color | shapeless colored feces | shaped colored feces |
| Ex. 12 | 140–160 | shaped no color | shapeless colored feces | shapeless colored feces |
| Ex. 13 | 120–140 | shaped some color | shapeless colored feces | shapeless colored feces |
| Ex. 14 | 140–160 | shaped no color | shapeless colored feces | shapeless colored feces |
| Ex. 15 | 150–180 | shaped some color | shapeless colored feces | shapeless colored feces |
| Ex. 16 | 130–150 | shaped no color | shapeless colored feces | shapeless colored feces |
| HP-55S | 125–130 | shapeless color*$^6$ | shapeless colored feces | shapeless colored feces |

Note:
*$^1$, Inventive Example;
*$^2$, shape of tablet remained;
*$^3$, shape of tablet did not remain;
*$^4$, contents slightly colored;
*$^5$, contents not colored;
*$^6$, contents colored As shown in Tables 1 and 2, the tablets which were coated with a coating material of the present invention were not disintegrated in small intestines, and dissolution of drugs contained in the tablets was not observed. In the large intestine, however, the coating materials of the present invention were disintegrated, and the drugs were released from the coated tablets.

When a polyester or copolymer of the present invention is used as a coating material or as an adjuvant of pharmaceutical preparations, and the resulting preparations are administered orally, drugs contained in the preparations are not decomposed or absorbed by digestive organs other than the large intestine, but instead are released selectively and therefore in a high concentration in the large intestine. This feature of the present invention makes it possible to design a dosage forms which have less side effects and improved drug bioavailability.

While the present invention has been described in detail and with reference to specific examples thereof, it will be apparent to one skilled in the art that various changes and modifications can be made therein without departing from the spirit and scope thereof.

What is claimed is:

1. A copolymer which comprises at least two structural units of the following formula (I'):

wherein R is a divalent organic group and R$^1$ is an oligosaccharide, wherein said oligosaccharide is unsubstituted or substituted with a moiety consisting of an acyl group, and has 2–10 saccharide residues, and is hydrolyzed and/or assimilated in the large intestine; and at least one structural unit of the following formula (II):

wherein R is a divalent organic group, each of $X^1$ and $X^2$ is independently an oxygen atom, an imino group or a sulfur atom and $R^2$ is selected from the group consisting of a saturated hydrocarbon having 2 to 20 carbon atoms, an unsaturated hydrocarbon having 4 to 20 carbon atoms, a polyalkylene, a polyalkylene glycol, a polyarylene oxide, a polyester and a polyamide when simultaneously R is phenylene and $R^1$ has 2 saccharide residues, the ratio of I':II in the copolymer is greater than 10:90.

2. The copolymer according to claim 1, wherein said oligosaccharide of $R^1$ is hydrolyzed by β-glycosidase, β-galactosidase or β-glucuronidase.

3. The copolymer according to claim 1, wherein the polyethylene glycol-based weight average molecular weight, as determined by gel permeation chromatography, of the copolymer is 2,000 to 1,000,000.

4. The copolymer according to claim 3, wherein the polyethylene glycol-based weight average molecular weight, as determined by gel permeation chromatography, of the copolymer is 5,000 to 500,000.

5. The copolymer according to claim 4, wherein the polyethylene glycol-based weight average molecular weight, as determined by gel permeation chromatography, of the copolymer is 5,000 to 100,000.

6. The copolymer according to claim 1, when R and $R^1$ are not simultaneously phenylene and two saccharide residues, respectively wherein the ratio of formula (I') to formula (II) in the copolymer is 1:99 to 99:1.

7. The copolymer according to claim 6, wherein the ratio of formula (I') to formula (II) in the copolymer is 5:95 to 80:20.

8. The copolymer according to claim 7, wherein the ratio of formula (I') to formula (II) in the copolymer is 10:90 to 70:30.

9. The copolymer according to claim 1, wherein said oligosaccharide has 2–5 saccharide residues.

10. The copolymer according to claim 1, wherein said oligosaccharide is digestible by an enzyme selected from the group consisting of β-glucosidase, β-galactosidase, β-glucuronidase, xylanse, β-glucanase, galactomannase, polygalacturonase, mucinase, chondroitin lyase, carboxymethylcellulase, cellulase and polygalacturonase lyase.

* * * * *